US00PP35848P2

(12) United States Plant Patent
Masor

(10) Patent No.: US PP35,848 P2
(45) Date of Patent: May 28, 2024

(54) COLEUS PLANT NAMED 'BALFLAMOBIN'

(50) Latin Name: *Plectranthus scutellarioides*
Varietal Denomination: Balflamobin

(71) Applicant: Ball Horticultural Company, West Chicago, IL (US)

(72) Inventor: Laura L. Masor, Buda, TX (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 18/516,511

(22) Filed: Nov. 21, 2023

(51) Int. Cl.
*A01H 5/12* (2018.01)
*A01H 6/50* (2018.01)

(52) U.S. Cl.
USPC ..... Plt./469
CPC ..... *A01H 6/50* (2018.05)

(58) Field of Classification Search
USPC ..... Plt./469
CPC ..... A01H 5/12
See application file for complete search history.

*Primary Examiner* — Kent L Bell
(74) *Attorney, Agent, or Firm* — Audrey Charles

(57) ABSTRACT

A new and distinct cultivar of *Coleus* plant named 'Balflamobin', characterized by its medium purplish-red and dark greyed-red colored foliage, and moderately vigorous, upright growth habit, is disclosed.

1 Drawing Sheet

Latin name of genus and species of plant claimed: *Plectranthus scutellarioides.*

Variety denomination: 'Balflamobin'.

BACKGROUND OF THE INVENTION

The present invention relates to a new and distinct cultivar of *Coleus* plant botanically known as *Plectranthus scutellarioides* and hereinafter referred to by the cultivar name 'Balflamobin'.

The new cultivar originated in a controlled breeding program in Arroyo Grande, California during July 2020. The objective of the breeding program was the development of *Coleus* cultivars with unique foliage coloration and leaf shape, upright growth habit, and good sun tolerance.

The new *Coleus* cultivar was the result of a self-pollination of STAINED GLASSWORKS Royalty 'UF16-88-9', U.S. Plant Pat. No. 30,585, characterized by its dark maroon with bright pink centers colored foliage, and vigorous, compact-upright growth habit. The new cultivar was selected as a single plant within the progeny of the above stated self-pollination during May 2021 in a controlled environment in Guadalupe, California.

Asexual reproduction of the new cultivar by terminal stem cuttings since May 2021 in Arroyo Grande, California and West Chicago, Illinois has demonstrated that the new cultivar reproduces true-to-type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balflamobin' as a new and distinct cultivar of *Coleus* plant:

1. Medium purplish-red and dark greyed-red colored foliage, and
2. Moderately vigorous, upright growth habit.

Plants of the new cultivar differ from plants of the parent primarily in having leaf and petiole pubescence and smaller sized foliage.

Of the many commercially available *Coleus* cultivars, the most similar in comparison to the new cultivar is Flame-Thrower Serrano 'UF15-6-28', U.S. Plant Pat. No. 30,970. However, in side-by-side comparisons, plants of the new cultivar differ from plants of 'UF15-6-28' in at least the following characteristics:

1. Plants of the new cultivar have a lighter shade of purplish-red leaf color than plants of 'UF15-6-28';
2. Plants of the new cultivar have smaller leaves than plants of 'UF15-6-28'; and
3. Plants of the new cultivar have greyed-red colored stems unlike the green-colored stems of plants of 'UF15-6-28'.

BRIEF DESCRIPTION OF THE PHOTOGRAPHS

The accompanying photographs show, as nearly true as it is reasonably possible to make the same in color illustrations of this type, the overall growth habit and typical foliage characteristics of the new cultivar. Colors in the photographs differ slightly from the color values cited in the detailed description, which accurately describes the colors of 'Balflamobin'. The approximately 3-month-old plants were grown in 3-gallon containers for approximately 8 weeks in an outdoor nursery in West Chicago, Ill. Treatments are described below in the Detailed Botanical Description.

DETAILED BOTANICAL DESCRIPTION

Figure 1:
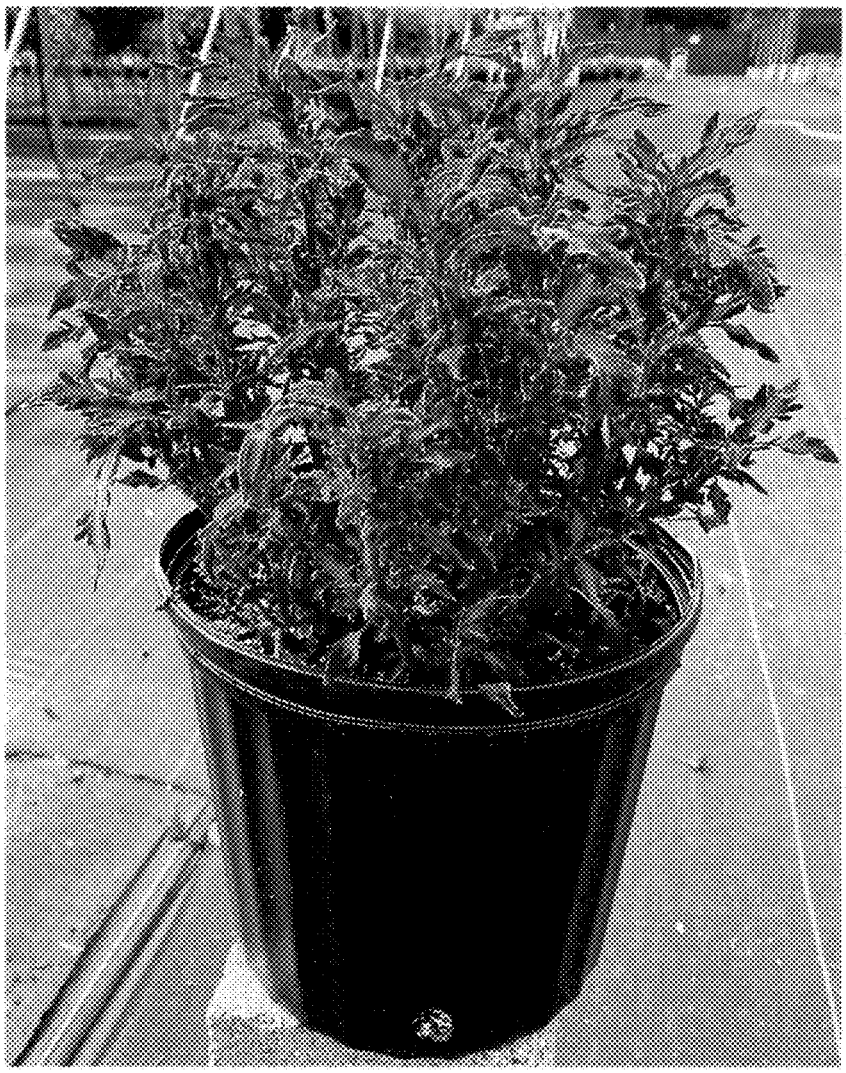
FIG. 1 illustrates a side view of the overall growth habit of 'Balflamobin'.
Figure 2:
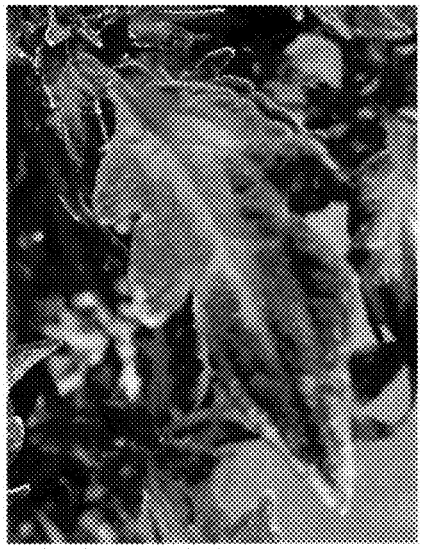
FIG. 2 illustrates a close-up view of leaves of 'Balflamobin'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The RHS Colour Chart of The Royal Horticultural Society, London, England, 2015 edition, except where general color terms of ordinary significance are used. The color values were determined in July 2023 under natural light conditions in West Chicago, Ill.

The following descriptions and measurements describe approximately 3-month-old plants produced from cuttings from stock plants and grown under conditions comparable to those used in commercial practice. The plants were grown in West Chicago, Illinois in 3-gallon pots utilizing a soilless growth medium for approximately 8 weeks in an outdoor nursery in West Chicago, Ill. Plants were given three pinches prior to transplant. Eight weeks after cuttings were stuck, plants were sprayed with growth regulators B-NINE (daminozide [butanedioic acid mono (2,2-dimethylhydrazide)]) at 2,500 ppm and CYCOCEL (chlormequat (2-chloroethyl) trimethylammonium chloride) at 800 ppm. Prior to transplant plants were grown in a polycarbonate greenhouse in West Chicago, Ill. Greenhouse temperatures were maintained at approximately 75° F. to 80° F. (24° C. to 27° C.) during the day and approximately 65° F. to 70° F. (18° C. to 21° C.) during the night. Supplemental lighting was used during propagation stage.

Measurements and numerical values represent averages of typical plants.

Botanical classification: *Plectranthus scutellarioides* 'Balflamobin'.

Parentage:

*Female and male parent.*—STAINED GLASSWORKS Royalty 'UF16-88-9', U.S. Plant Pat. No. 30,585.

Propagation:

*Type cutting.*—Terminal stem.

*Time to initiate roots.*—Approximately 4 to 6 days.

*Time to produce a rooted cutting.*—Approximately 14 to 21 days.

*Root description.*—Fibrous.

*Rooting habit.*—Freely branching.

Plant description:

*Commercial crop time.*—Approximately 5 to 7 weeks from a rooted cutting to finish in a 10 cm pot.

*Growth habit and general appearance.*—Moderately vigorous, upright.

*Size.*—Height from soil level to top of plant plane: Approximately 29.0 cm. Width: Approximately 35.0 cm.

*Branching habit.*—Freely branching, pinching not required but improves basal branching. Quantity of lateral branches per plant: Approximately 20.

*Branch.*—Strength: Strong. Shape: Oval in cross section. Length: Approximately 25.0 cm. Diameter at central internode: Approximately 5.0 mm. Length of central internode: Approximately 2.5 cm. Texture: Dense minute pubescence. Color of young and mature stems: 187A.

Foliage description:

*General description.*—Quantity of leaves per lateral branch: Approximately 12. Fragrance: None. Form: Simple. Arrangement: Opposite.

*Leaves.*—Aspect: Petiole is at an acute angle to stem; leaf blade is perpendicular to stem, and transitions to an obtuse angle with age. Appearance: Matte. Shape: Elliptic to ovate. Margin: Lobed. Apex: Acute. Base: Attenuate. Venation pattern: Pinnate. Length of mature leaf: Approximately 4.5 cm. Width of mature leaf: Approximately 2.0 cm. Texture of upper surface: Densely pubescent. Texture of lower surface: Moderately pubescent with dense pubescence on venation. Pubescence color: A mixture of colorless, transparent and 187A. Color of upper surface of young and mature foliage: Irregularly shaped centers of 64B to 64C occasionally mottled with 161A; area surrounding centers to margins of 187A occasionally mottled with 146B; venation coloration in centers of 64A to 64B other areas indistinguishable from leaf lamina. Color of lower surface of young and mature foliage: Irregular centers of 187D with area surrounding centers to margins of 187A; venation coloration indistinguishable from leaf lamina.

*Petiole.*—Length: Approximately 1.5 cm. Width: Approximately 2.0 mm. Texture: Dense minute pubescence. Color: 186D.

Flowering description: To date, flower development has not been observed on plants of the new *Coleus*.

Disease and pest resistance: To date, resistance to pathogens and pests common to *Coleus* has not been observed.

What is claimed is:

1. A new and distinct cultivar of *Coleus* plant named 'Balflamobin', substantially as herein illustrated and described.

* * * * *